United States Patent
Möckel et al.

(10) Patent No.: US 6,913,910 B2
(45) Date of Patent: Jul. 5, 2005

(54) NUCLEOTIDE SEQUENCES CODING FOR THE GLK-GENE

(75) Inventors: Bettina Möckel, Düsseldorf (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 153 days.

(21) Appl. No.: 10/197,541

(22) Filed: Jul. 18, 2002

(65) Prior Publication Data

US 2003/0022320 A1 Jan. 30, 2003

Related U.S. Application Data

(62) Division of application No. 09/725,898, filed on Nov. 30, 2000, now abandoned.

(30) Foreign Application Priority Data

Dec. 2, 1999 (DE) .......................... 199 58 159

(51) Int. Cl.⁷ .......................... C12N 15/00; C12N 1/20; C12P 13/08; C12P 13/04; C07H 21/04
(52) U.S. Cl. .................... 435/115; 435/106; 435/252.3; 435/320.1; 536/23.2; 536/23.1
(58) Field of Search ................................ 435/115, 106, 435/252.3, 320.1; 536/23.1, 23.2

(56) References Cited

U.S. PATENT DOCUMENTS

| 5,935,934 | A | 8/1999 | Vegeto et al. | |
| 6,316,232 | B1 * | 11/2001 | Sprenger et al. | ............ 435/156 |
| 6,361,986 | B1 * | 3/2002 | Tilg et al. | ................... 435/194 |

FOREIGN PATENT DOCUMENTS

| DE | 19644567 | * | 4/1998 |
| EP | 0 197 335 | | 10/1986 |
| EP | 1 108 790 | | 6/2001 |
| WO | WO 99 55877 | | 11/1999 |
| WO | WO 01 00844 | | 1/2001 |

OTHER PUBLICATIONS

Lee et al., "Characterization of glk, a gene coding for glucose kinase of *Corynebacterium glutamicum*", Abstracts of the General Meeting of the American Society for Microbiology, Bd. 99, 1999, p. 369, XP000990824.

Enright M. C., "*Streptococcus pneumoniae* gki gene (allele 23)", Database EMBL, Nov. 1998.

Park Sun–Yang et al., "Characterization of glk, a gene coding for glucose kinase of *Corynebacterium glutamicum*", FEMS Microbiology Letters, Bd. 188, Nr. 2, 2000, p. 209–215.

Park S Y et al, "*Corynebacterium glutamicum* glucose kinease (glk) gene, complete cds; and unknown genes", Database EMBL, Jul. 2000.

Bibb M., "*S. coelicolor* glk gene for glucose kinase", Database EMBL, May 1992.

Snoep Jacky et al., "Reconstitution of glucose uptake and phosphorylation in a glucose–negative mutant of *E. coli* by using *Zymomonas mobilis* genes encoding the glucose facilitator protein and glucokinase", Journal of Bacteriology, Bd. 176, Nr. 7, 1994, p. 2133–2135.

* cited by examiner

*Primary Examiner*—Maryam Monshipouri
(74) *Attorney, Agent, or Firm*—Pillsbury Winthrop Shaw Pittman LLP

(57) ABSTRACT

The invention relates to an isolated polynucleotide containing a polynucleotide sequence selected from the group comprising:
  a) polynucleotide that is at least 70% identical to a polynucleotide coding for a polypeptide that contains the amino acid sequence of SEQ ID No. 2,
  b) polynucleotide coding for a polypeptide that contains an amino acid sequence that is at least 70% identical to the amino acid sequence of SEQ ID No.2,
  c) polynucleotide that is complementary to the polynucleotides of a) or b), and
  d) polynucleotide containing at least 15 successive bases of the polynucleotide sequence of a), b) or c), and processes for the fermentative production of L-amino acids by enhancement of the glk-gene coding for the enzyme glucokinase.

10 Claims, 2 Drawing Sheets

Fig. 1: Plasmid pEC-K18mob2
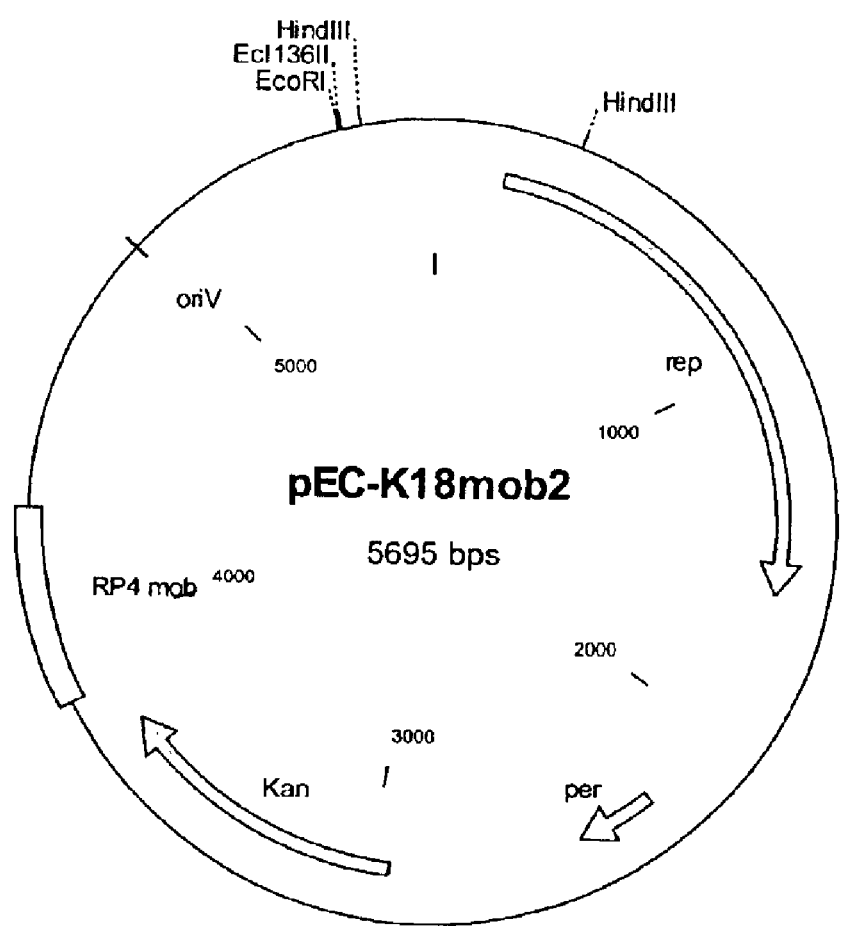

Fig. 2: Plasmid pEC-K-18mob2glkexp
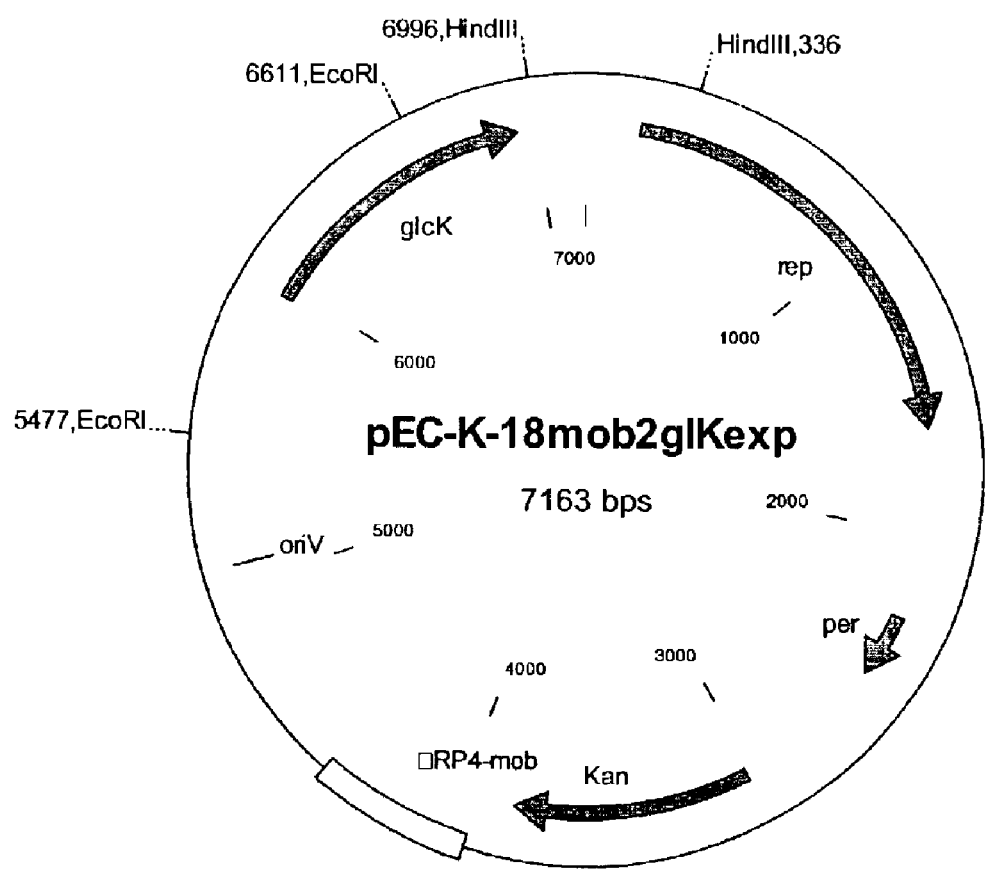

NUCLEOTIDE SEQUENCES CODING FOR THE GLK-GENE

This application is a Divisional of U.S. application Ser. No. 09/725,898, filed Nov. 30, 2000, now abandoned.

The invention provides nucleotide sequences coding for the glk-gene and processes for the fermentative production of L-amino acids, in particular L-lysine, using coryneform bacteria in which the glk-gene is enhanced.

PRIOR ART

L-amino acids, in particular L-lysine, are used in human medicine and in the pharmaceutical industry, but especially in animal nutrition.

It is known that L-amino acids can be produced by fermentation of strains of coryneform bacteria, in particular *Corynebacterium glutamicum*. On account of the great importance of amino acids efforts are constantly being made to improve the production processes. Improvements in production processes may involve fermentation technology measures, such as for example stirring and provision of oxygen, or the composition of the nutrient media, such as for example the sugar concentration during fermentation, or the working-up to the product form by for example ion exchange chromatography, or the intrinsic output properties of the microorganism itself.

Methods involving mutagenesis, selection and choice of mutants are used to improve the output properties of these microorganisms. In this way strains are obtained that are resistant to antimetabolites, such as for example the lysine-analogon S-(2-aminoethyl)-cysteine or that are auxotrophic for regulatorily important metabolites and produce L-amino acids such as for example L-lysine.

For some years recombinant DNA technology methods have also been used to improve strains of *Corynebacterium* producing L-amino acids, by amplifying individual biosynthesis genes for L-amino acids and investigating the effect on the production of L-amino acids. Review articles on this topic may be found in, inter alia, Kinoshita ("Glutamic Acid Bacteria", in: Biology of Industrial Microorganisms, Demain and Solomon (Eds.), Benjamin Comings, London, UK, 1985, 115–142), Hilliger (BioTec 2, 40–44 (1991)), Eggeling (Amino Acids 6:261–272 (1994)), Jetten and Sinskey (Critical Reviews in Biotechnology 15, 73–103 (1995)) and Sahm et al. (Annuals of the New York Academy of Science 782, 25–39 (1996)).

OBJECT OF THE INVENTION

The inventors have set themselves the task of providing new measures for improving the fermentative production of L-amino acids, in particular L-lysine.

DESCRIPTION OF THE INVENTION

L-amino acids, in particular L-lysine, are used in human medicine, in the pharmaceutical industry and in particular in animal nutrition. It is therefore of general interest to provide new improved processes for the production of L-amino acids, in particular L-lysine.

Wherever L-lysine or lysine are mentioned hereinafter, this should be understood to mean not only the bases per se but also the salts, for example lysine monohydrochloride or lysine sulfate.

The invention provides an isolated polynucleotide obtained from coryneform bacteria, containing a polynucleotide sequence selected from the following group a) polynucleotide that is at least 70% identical to a polynucleotide coding for a polypeptide that contains the amino acid sequence of SEQ ID No. 2,
b) polynucleotide coding for a polypeptide, that contains an amino acid sequence that is at least 70% identical to the amino acid sequence of SEQ ID No. 2,
c) polynucleotide that is complementary to the polynucleotides of a) or b), and
d) polynucleotide containing at least 15 successive nucleotides of the polynucleotide sequence of a), b) or c).

The invention also provides a polynucleotide that is preferably a recombinant DNA replicable in coryneform bacteria.

The invention likewise provides a polynucleotide that is an RNA.

The invention moreover provides a polynucleotide according to claim 1 wherein the polynucleotide is preferably a replicable DNA containing:
(i) the nucleotide sequenece shown in SEQ ID No. 1, or
(ii) at least one sequence that corresponds to the sequence (i) within the region of degeneration of the genetic code, or
(iii) at least one sequence that hybridises with the sequence that is complementary to the sequence (i) or (ii), and optionally
(iv) functionally neutral sense mutations in (i).

The invention in addition provides:
a vector containing the polypeptide according to claim 1, and coryneform bacteria serving as host cell that contain the said vector.

The invention moreover provides polynucleotides that substantially comprise a polynucleotide sequence, that can be obtained by screening by means of hybridisation of a corresponding gene library that contains the complete gene with the polynucleotide sequence corresponding to SEQ ID No. 1 with a probe that contains the sequence of the aforementioned polynucleotide according to SEQ ID No. 1 or a fragment thereof, and isolation of the aforementioned DNA sequence.

Polynucleotide sequences according to the invention are suitable as hybridisation probes for RNA, cDNA and DNA in order to isolate in full length cDNA that code for glucokinase and to isolate such cDNA or genes that have a high degree of similarity to the sequence of the glucokinase gene.

Polynucleotide sequences according to the invention are furthermore suitable as primers for producing DNA of genes that code for glucokinase, by the polymerase chain reaction (PCR).

Such oligonucleotides serving as probes or primers contain at least 30, preferably at least 20, and most particularly preferably at least 15 successive bases. Oligonucleotides with a length of at least 40 or 50 nucleotides are also suitable.

"Isolated" means separated from its natural environment.

"Polynucleotide" refers in general to polyribonucleotides and polydeoxyribonucleotides, in which connection these terms may refer to unmodified RNA or DNA or modified RNA or DNA.

By the term "polypeptides" are understood peptides or proteins that contain two or more amino acids bound via peptide bonds.

The polypeptides according to the invention include a polypeptide according to SEQ ID No. 2, in particular those having the biological activity of glucokinase as well as those that are at least 70% identical to the polypeptide according to SEQ ID No. 2, preferably at least 80% and particularly [sic] at least 90% to 95% identical to the polypeptide according to SEQ ID No. 2 and that have the aforementioned activity.

The invention furthermore relates to a process for the fermentative production of L-amino acids, in particular L-lysine, using coryneform bacteria that in particular already produce an L-amino acid, and in which the nucleotide sequences coding for the glk-gene are enhanced, in particular are overexpressed.

The term "enhancement" describes in this connection increasing the intracellular activity of one or more enzymes in a microorganism that are coded by the corresponding DNA, by for example increasing the number of copies of the gene and/or genes, using a strong promoter or using a gene that codes for a corresponding enzyme having a high activity, and optionally combining these measures.

The microorganisms that are the subject of the present invention can produce amino acids, in particular L-lysine, from glucose, sucrose, lactose, fructose, maltose, molasses, starch, cellulose or from glycerol and ethanol. The microorganisms may be types of coryneform bacteria, in particular of the genus *Corynebacterium*. In the genus *Corynebacterium* there should in particular be mentioned the type *Corynebacterium glutamicum*, which is known to those in the specialist field for its ability to produce L-amino acids.

Suitable strains of the genus *Corynebacterium*, in particular of the type *Corynebacterium glutamicum*, are for example the following known wild type strains:

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965
*Brevibacterium flavum* ATCC14067
*Brevibacterium lactofermentum* ATCC13869 and
*Brevibacterium divaricatum* ATCC14020 and mutants and/or strains obtained therefrom that produce L-amino acids, such as for example

*Corynebacterium glutamicum* FERM-P 1709
*Brevibacterium flavum* FERM-P 1708
*Brevibacterium lactofermentum* FERM-P 1712
*Corynebacterium glutamicum* FERM-P 6463
*Corynebacterium glutamicum* FERM-P 6464 and
*Corynebacterium glutamicum* DSM5715.

The inventors have succeeded in isolating the new glk-gene from *C. glutamicum* coding for the enzyme glucokinase (EC 2.7.1.2).

In order to isolate the glk-gene or also other genes from *C. glutamicum*, a gene library of this microorganism is first of all cultivated in *E. coli*. The cultivation of gene libraries is described in generally known textbooks and handbooks. By way of example there may be mentioned the textbook by Winnacker: Gene und Klone, Eine Einführung in die Gentechnologie (Genes and Clones, An Introduction to Gene Technology) (Verlag Chemie, Weinheim, Germany, 1990) or the handbook by Sambrook et al.: Molecular Cloning, A Laboratory Manual (Cold Spring Harbor Laboratory Press, 1989). A very well-known gene library is that of the *E. coli* K-12 strain W3110, which has been cultivated by Kohara et al. (Cell 50, 495–508 (1987)) in λ-vectors. Bathe et al. (Molecular and General Genetics, 252:255–265, 1996) describe a gene library from *C. glutamicum* ATCC13032 that has been cultivated with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575). Bormann et al. (Molecular Microbiology 6(3), 317–326 (1992)) in turn describe a gene library obtained from *C. glutamicum* ATCC13032 using the cosmid pHC79 (Hohn and Collins, Gene 11, 291–298 (1980)). In order to produce a gene library from *C. glutamicum* in *E. coli*, plasmids such as pBR322 (Bolivar, Life Sciences, 25, 807–818 (1979)) or pUC9 (Vieira et al., 1982, Gene, 19:259–268) may also be used. Particularly suitable as hosts are those *E. coli* strains that are restriction-defective and recombinant-defective. An example of such strains is the strain DH5αmcr that has been described by Grant et al. (Proceedings of the National Academy of Sciences USA, 87 (1990) 4645–4649). The long DNA fragments cloned with the aid of cosmids may then be sub-cloned in turn in suitable vectors available for the sequencing and finally sequenced, such as is described for example by Sanger et al. (Proceedings of the National Academy of Sciences of the United States of America, 74:5463–5467, 1977).

In this way the new DNA sequence of *C. glutamicum* coding for the gene glk was obtained which, as SEQ ID No. 1, is a subject of the present invention. Furthermore the amino acid sequence of the corresponding protein was derived from the present DNA sequence using the methods described above. The amino acid sequence of the glk-gene product that is obtained is shown in SEQ ID No. 2.

Coding DNA sequences that are obtained from SEQ ID NO. 1 due to the degeneracy of the genetic code are likewise a subject of the invention. In the specialist field conservative amino acid exchanges, such as for example the exchange of glycine by alanine or of aspartic acid by glutamic acid in proteins are furthermore known as sense mutations that do not lead to any fundamental change in the activity of the protein, i.e. that are functionally neutral. It is furthermore known that changes at the N- and/or C-terminus of a protein do not substantially affect, or may even stabilise, its function. The person skilled in the art may find information on this in, inter alia, Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences that are obtained in a corresponding manner from SEQ ID NO. 2 and DNA sequences coding for these amino acid sequences are similarly a subject of the invention.

In the same way DNA sequences that hybridise with SEQ ID NO. 1 or parts of SEQ ID NO. 1 are subjects of the invention. Finally, DNA sequences that are produced by the polymerase chain reaction (PCR) using primers that are formed from SEQ ID NO. 1 are also a subject of the invention. Such oligonucleotides typically have a length of at least 15 nucleotides.

The person skilled in the art will find information on identifying DNA sequences by means of hybridisation in, inter alia, the handbook "The DIG System User's Guide for Filter Hybridization" published by Boehringer Mannheim GmbH (Mannheim, Germany, 1993) and in Liebl et al. (International Journal of Systematic Bacteriology (1991) 41: 255–260). The person skilled in the art can find details of the amplification of DNA sequences by means of the polymerase chain reaction (PCR) in, inter alia, the handbook by Gait: Oligonucleotide synthesis: A Practical Approach (IRL Press, Oxford, UK, 1984) and in Newton and Graham: PCR (Spektrum Akademischer Verlag, Heidelberg, Germany, 1994).

The inventors have found that coryneform bacteria produce L-amino acids, in particular L-lysine, in an improved manner after overexpression of the glk-gene.

In order to achieve an overexpression the number of copies of the corresponding genes can be increased, or the promoter and regulation region or the ribosome binding site that is located upstream of the structure gene can be mutated. Expression cassettes that are incorporated upstream of the structure gene act in the same way. It is in addition possible by means of inducible promoters to increase the expression during the course of the fermentative production of L-amino acid. The expression is similarly improved by measures adopted to increase the lifetime of the m-RNA. Furthermore, the enzyme activity is likewise increased by preventing the decomposition of the enzyme protein. The genes or gene constructs may be present either in plasmids with different numbers of copies or may be integrated and amplified in the chromosome. Alternatively, an overexpression of the relevant genes may be achieved by changing the composition of the medium and cultivation conditions.

The person skilled in the art may find details of this in, inter alia, Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent specification EPS 0 472 869, in U.S. Pat. No. 4,601,893, in Schwarzer and Pühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese published patent application JP-A-10-229891, in Jensen and Hammer (Biotechnology and Bioengineering 58, 191–195 (1998)), in Makrides (Microbiological Reviews 60:512–538 (1996)) and in known textbooks on genetics and molecular biology.

For example, the glk-gene according to the invention was overexpressed by means of plasmids.

Suitable plasmids are those that are replicated in coryneform bacteria. Numerous known plasmid vectors, such as for example pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as for example those that are based on pCG4 (U.S. Pat. No. 4,489,160) or pNG2 (Serwold-Davis et al., FEMS Microbiology Letters 66, 119–124 (1990)) or pAG1 (U.S. Pat. No. 5,158,891) may be used in the same way.

Also suitable are those plasmid vectors by means of which the process of gene amplification by integration into the chromosome can be employed, as has been described for example by Reinscheid et al. (Applied and Environmental Microbiology 60, 126–132 (1994)) for the duplication and/or amplification of the hom-thrB-operon. In this method the full gene is cloned in a plasmid vector that can replicate in a host (typically E. coli) but not in C. glutamicum. Suitable vectors that may be mentioned are for example pSUP301 (Simon et al., Bio/Technology 1, 784–791 (1983)), pK18mob or pK19mob (Schafer et al., Gene 145, 69–73 (1994)), pGEM-T (Promega corporation, Madison, Wis., USA), pCR2.1-TOPO (Shuman (1994), Journal of Biological Chemistry 269:32678–84; U.S. Pat. No. 5,487,993), pCR®Blunt (Firma Invitrogen, Groningen, Netherlands; Bernard et al., Journal of Molecular Biology, 234: 534–541 (1993)) or pEM1 (Schrumpf et al, 1991, Journal of Bacteriology 173:4510–4516). The plasmid vector that contains the gene to be amplified is then transferred by conjugation or transformation into the desired strain of C. glutamicum.

The method of conjugation is described for example by Schafer et al. (Applied and Environmental Microbiology 60, 756–759 (1994)). Methods of transformation are described for example in Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a crossover event, the resulting strain contains at least two copies of the relevant gene.

The invention accordingly also provides a process for the fermentative production of L-amino acids, in particular L-lysine, in which a strain transformed with a plasmid vector is used, and the plasmid vector carries the nucleotide sequence of the gene coding for the enzyme glucokinase.

In addition it may be advantageous for the production of L-amino acids, in particular L-lysine, to enhance, as well as the glk-gene, further genes of the biosynthesis pathway of the desired L-amino acid so that one or more enzymes of the relevant biosynthesis pathway, glycolysis, anaplerotic, citric acid cycle or of the amino acid export is overexpressed.

Thus, the following may for example be overexpressed for the production of L-lysine:
  at the same time the dapA-gene coding for dihydrodipicolinate synthase (EP-B 0 197 335), or
  at the same time an lysC-gene coding for a feedback-resistant aspartate kinase (Kalinowski et al. (1990), Molecular and General Genetics 224: 317–324), or
  at the same time the gap-gene coding for glyceraldehyde-3-phosphate-dehydrogenase (Eikmanns (1992), Journal of Bacteriology 174:6076–6086), or
  at the same time the tpi-gene coding for triosephosphate isomerase (Eikmanns (1992), Journal of Bacteriology 174:6076–6086), or
  at the same time the pgk-gene coding for 3-phosphate glycerate kinase (Eikmanns (1992), Journal of Bacteriology 174:6076–6086), or
  at the same time the pyc-gene coding for pyruvate carboxylase (Eikmanns (1992), Journal of Bacteriology 174:6076–6086), or
  at the same time the mqo-gene coding for malate-quinone-oxidoreduktase (Molenaar et al., European Journal of Biochemistry 254, 395–403 (1998)), or
  at the same time the lysE-gene coding for lysine export (DE-A-195 48 222).

Furthermore, it may be advantageous for the production of L-amino acids, in particular L-lysine, to attenuate in addition to the glk-gene the following at the same time:
  the pck-gene coding for phosphoenolpyruvate carboxykinase (DE 199 50 409.1; DSM 13047) and/or
  the pgi-gene coding for glucose-6-phosphate isomerase (U.S. Ser. No. 09/396,478; DSM 12969).

Furthermore it may be advantageous for the production of L-amino acids, in particular L-lysine, in addition to the overexpression of the glk-gene, to switch off undesirable secondary reactions (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms produced according to the invention may be cultured continuously or batchwise in a batch process (batch cultivation) or in a fed batch or repeated fed batch process in order to produce L-amino acids, in particular L-lysine. An overview of known cultivation methods is given in the textbook by Chmiel (Bioprozesstechnik 1. Einfuhrung in die Bioverfahrenstechnik)(Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must suitably satisfy the requirements of the relevant strains. Descriptions of culture media for various microorganisms are given in the handbook "Manual of Methods for General Bacteriology" of the American Society for Bacteriology (Washington D.C., USA, 1981). As carbon source there may be used sugars and carbohydrates such as for example glucose, sucrose, lactose, fructose, maltose, molasses, starch and cellulose, oils and fats such as for example soya bean oil, sunflower oil, groundnut oil and coconut oil, fatty acids such as for example palmitic acid, stearic acid and linoleic acid, alcohols such as for example glycerol, ethanol, and organic acids such as for example acetic acid. These substances may be used individually or as a mixture. As nitrogen source there may be used organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources may be used individually or as a mixture. As phosphorus source there may be used phosphoric acid, potassium dihydrogen phosphate or dipotassium hydrogen phosphate, or the corresponding sodium-containing salts. The culture medium must furthermore contain salts of metals such as for example magnesium sulfate or iron sulfate that are necessary for growth. Finally, essential growth substances such as amino acids and vitamins may be used in addition to the substances mentioned above. Apart from this, suitable precursors may be added to the culture medium. The aforementioned feedstock substances may be added to the culture in the form of a single batch, or may be metered in in a suitable way during the cultivation.

Alkaline compounds such as sodium hydroxide, potassium hydroxide, ammonia or ammonia water or acidic compounds such as phosphoric acid or sulfuric acid may be used in an appropriate manner in order to regulate the pH of the culture. Antifoaming agents such as for example fatty acid polyglycol esters may be used to regulate foam formation. Suitable selectively acting substances such as for example antibiotics may be added to the medium in order to maintain the stability of plasmids. Oxygen or oxygen-containing gas mixtures such as for example air are introduced into the culture in order to maintain aerobic conditions. The temperature of the culture is normally 20° C. to 45° C. and preferably 25° C. to 40° C. The culture is continued until a maximum yield of lysine has been formed. This target is normally achieved within 10 hours to 160 hours.

The invention accordingly also provides a process for the fermentative production of L-amino acids, in particular L-lysine, in which the following steps are carried out:
a) fermentation of coryneform bacteria producing the L-amino acid, in which at least the gene coding for the enzyme glucokinase is enhanced, in particular is overexpressed,
b) enrichment of the L-amino acid in the medium or in the cells of the bacteria, and
c) isolation of the L-amino acid.

The analysis of the L-lysine may be carried out by anion exchange chromatography followed by ninhydrin derivatisation, as described for example by Spackman et al. (Analytical Chemistry, 30, (1958), 1190).

The process according to the invention serves for the fermentative production of L-amino acids, in particular L-lysine.

BRIEF DECSRIPTION OF THE DRWAINGS

FIG. 1: Map of the plasmid pEC-K18mob2.

FIG. 2: Map of the plasmid pEC-K18mob2glkexp.

EXAMPLES

The present invention is illustrated in more detail hereinafter with the aid of embodiment examples.

Example 1
Production of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partially cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Molecular Biochemicals, Mannheim, Germany, Product Description SAP, Code no. 1758250). The DNA of the cosmid vector SuperCos1 (Wahl et al. (1987) Proceedings of the National Academy of Sciences, USA 84:2160–2164), obtained from Stratagene (La Jolla, USA, Product Description SuperCos1 Cosmid Vector Kit, Code no. 251301), was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid-DNA was then cleaved with the restriction enzyme BamHI (Amersham Pharmacia, Freiburg, Germany, Product Description BamHI, Code no. 27-0868-04). The cosmid-DNA treated in this way was mixed with the treated ATCC13032-DNA and the batch was treated with T4-DNA-ligase (Amersham Pharmacia, Freiburg, Germany, Product Description T4-DNA-ligase, Code no. 27-0870-04). The ligation mixture was then packed in phages with the aid of the Gigapack II XL Packing Extracts (Stratagene, La Jolla, USA, Product Description Gigapack II XL Packing Extract, Code no. 200217). In order to infect the *E. coli* strain NM554 (Raleigh et al. 1988, Nucleic Acid Research 16:1563–1575) the cells were taken up in 10 mM $MgSO_4$ and mixed with an aliquot of the phage suspension. Infection and titration of the cosmid bank were carried out as described by Sambrook et al. (1989, Molecular Cloning: A Laboratory Manual, Cold Spring Harbor), the cells having been plated out on LB-agar (Lennox, 1955, Virology, 1:190) with 100 µg/ml ampicillin. Recombinant individual clones were selected after incubation overnight at 37° C.

Example 2
Isolation and Sequencing of the glk-Gene

The cosmid-DNA of an individual colony was isolated using the Qiaprep Spin Miniprep Kit (Product No. 27106, Qiagen, Hilden, Germany) according to the manufacturer's instructions and partially cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Molecular Biochemicals, Mannheim, Germany, Product Description SAP, Product No. 1758250). After gel electrophoresis separation the cosmid fragments were isolated in the large region from 1500 to 2000 bp using the QiaExII Gel Extraction Kit (Product No. 20021, Qiagen, Hilden, Germany). The DNA of the sequencing vector pZero-1 obtained from Invitrogen (Groningen, Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture having been incubated overnight with T4-ligase (Pharmacia Biotech, Freiburg, Germany). This ligation mixture was electroporated into the *E. coli* strain DH5αMCR (Grant, 1990, Proceedings of the National Academy of Sciences U.S.A., 87:4645–4649) (Tauch et al. 1994, FEMS Microbiol Letters, 123:343–7) and was plated out on LB-agar (Lennox, 1955, Virology, 1:190) with 50 µg/ml zeocin. The plasmid preparation of the recombinant clones was performed with Biorobot 9600 (Product No. 900200, Qiagen, Hilden, Germany). The sequencing was carried out according to the dideoxy chain termination method of Sanger et al. (1977, Proceedings of the National Academies of Sciences U.S.A., 74:5463–5467) as modified by Zimmermann et al. (1990, Nucleic Acids Research, 18:1067). The RR dRhodamine Terminator Cycle Sequencing Kit from PE Applied Biosystems(Product No. 403044, Weiterstadt, Germany) was used. The gel electrophoresis separation and analysis of the sequencing reaction was performed in a rotiphoresis NF acrylamide/bisacrylamide gel (29:1) (Product No. A124.1, Roth, Karlsruhe, Germany) together with the ABI Prism 377 sequencing equipment from PE Applied Biosystems (Weiterstadt, Germany).

The raw sequence data obtained were then processed using the Staden program package (1986, Nucleic Acids Research, 14:217–231) Version 97-0. The individual sequences of the pZero1 derivates were assembled into a coherent Contig. The computer-assisted analysis of the coding region was performed with the program XNIP (Staden, 1986, Nucleic Acids Research, 14:217–231). Further analyses were carried out with the BLAST search programs (Altschul et al., 1997, Nucleic Acids Research, 25:3389–3402), against the non-redundant data bank of the National Center for Biotechnology Information (NCBI, Bethesda, Md., USA).

The obtained nucleotide sequence is shown in SEQ ID No. 1. Analysis of the nucleotide sequence revealed an open reading frame of 969 base pairs, which was termed the glk-gene. The glk-gene codes for a protein of 323 amino acids.

Example 3

Production of a Shuttle Vector pEC-K18mob2glkexp for Enhancing the glk-Gene in *C. glutamicum*

3.1. Cloning of the glk-Gene

Chromosomal DNA was isolated from the strain ATCC 13032 according to the method of Eikmanns et al. (Microbiology 140: 1817–1828 (1994)). On the basis of the sequence of the glk-gene known for *C. glutamicum* from Example 2 the following oligonucleotides were selected for the polymerase chain reaction:

glk-ex1:
5' ACT GAG GTG AGC CAG AAC 3' (SEQ ID NO:3)
glk-ex2:
5' GAT CTA TCT AGA CAC CTA GTT GGC TTC CAC 3' (SEQ ID NO:4)

The illustrated primers were synthesised by ARK Scientific GmbH Biosystems (Darmstadt, Germany) and the PCR reaction was carried out according to the standard PCR method of Innis et al. (PCR protocols. A Guide to Methods and Applications, 1990, Academic Press) with Pwo polymerase from Roche Diagnostics GmbH (Mannheim, Germany). With the aid of the polymerase chain reaction the primers permit the amplification of a ca. 1.45 kb size DNA fragment which carries the glk-gene with the potential promoter region. The DNA sequence of the amplified DNA fragment was checked by sequencing.

3.2. Production of the *E. coli—C. glutamicum* Shuttle Vector pEC-K18mob2

The *E. coil—C. glutamicum* shuttle vector was constructed according to the prior art. The vector contains the replication region rep of the plasmid pGA1 including the replication effector per (U.S. Pat. No. 5,175,108; Nesvera et al., Journal of Bacteriology 179, 1525–1532 (1997)), the aph(3')-IIa-gene of the transposon Tn5 imparting resistance to kanamycin (Beck et al., Gene 19, 327–336 (1982)), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander, J. M. et al., Gene 26, 101–106 (1983)) and the mob region of the plasmid RP4 (Simon et al., Bio/Technology 1:784–791 (1983)). The constructed vector was transformed into the *E. coli* strain DH5α (Hanahan, In: DNA Cloning. A Practical Approach. Vol. I, IRL-Press, Oxford, Washington D.C., USA). The selection of plasmid-carrying cells was made by plating out the transformation batch onto LB agar (Sambrook et al., Molecular cloning: A Laboratory Manual. 2$^{nd}$ Ed. Cold Spring Harbor Laboratory Press, Cold Spring Harbor, N.Y.) that had been supplemented with 25 mg/l kanamycin. Plasmid DNA was isolated from a transformant using the QIAprep Spin Miniprep Kit from Qiagen and was checked by restriction with the restriction enzyme EcoRI and HindIII followed by agarose gel electrophoresis (0.8%). The plasmid was named pEC-K18mob2 and is shown in FIG. 1.

The following microorganism was filed at the German Collection of Microorganisms and Cell Cultures (DSMZ, Brunswick, Germany) according to the Budapest Convention:

*C. glutamicum* strain DSM 5715/pEC-K18mob2 as DSM 13245

3.3. Cloning of glk in the *E. coli—C. glutamicum* Shuttle Vector pEC-K18mob2

The *E. coil—C. glutamicum* shuttle vector pEC-K18mob2 described in Example 3.2 was used as vector. DNA of this plasmid was completely cleaved with the restriction enzyme Ecl136II and then dephosphorylated with shrimp alkaline phosphatase (Roche Diagnostics GmbH, Mannheim, Germany, Product Description SAP, Product No. 1758250).

The glk fragment obtained as described in Example 3.1 was mixed with the prepared vector pEC-K18mob2 and the batch was treated with T4-DNA-ligase (Amersham Pharmacia, Freiburg, Germany, Product Description T4-DNA-Ligase, Code no. 27-0870-04). The ligation batch was transformed into the *E. coli* strain DH5αmcr (Grant, 1990, Proceedings of the National Academy of Sciences U.S.A., 87:4645–4649). The selection of plasmid-carrying cells was made by plating out the transformation batch onto LB-agar (Lennox, 1955, Virology, 1:190) with 25 mg/l of kanamycin. Recombinant individual cells were selected after incubation overnight at 37° C. Plasmid DNA was isolated from a transformant using the Qiaprep Spin Miniprep Kit (Product No. 27106, Qiagen, Hilden, Germany) according to the manufacturer's instructions and cleaved with the restriction enzymes EcoRI and XbaI in order to check the plasmid by subsequent agarose gel electrophoresis. The plasmid obtained was named pEC-K18mob2glkexp and is shown in FIG. 2.

Example 4

Transformation of the Strain *Corynebacterium glutamicum* RES167 with the Plasmid pEC-K18mob2glkexp.

The strain *C. glutamicum* RES167 (Schafer, A. et al., Journal Bacteriological 176: 7309–731(1994)) was transformed with the plasmid pEC-K18mob2glkexp using the electroporation method described by Liebl et al., (FEMS Microbiology Letters, 53:299–303 (1989)). The selection of the tranformants was made on LBHIS agar consisting of 18.5 g/l brain-heart infusion broth, 0.5 M sorbitol, 5 g/l Bacto-Trypton, 2.5 g/l Bacto-Yeast Extract, 5 g/l NaCl and 18 g/l Bacto-Agar, that had been supplemented with 25 mg/l kanamycin. Incubation was carried out at 33° C. for two days.

Plasmid DNA was isolated from a transformant by the usual methods (Peters-Wendisch et al., Microbiology, 144:915–927 (1998)), cleaved with the restriction endonucleases EcoRI and XbaI, and the plasmid was checked by subsequent agarose gel electrophoresis. The strain obtained was named C. glutamicum RES167/pEC-K18mob2glkexp.

Example 5

Production of Lysine

The strain C. glutamicum RES167/pEC-K18mob2glkexp obtained in Example 4 was cultivated in a nutrient medium suitable for producing lysine, and the lysine content in the culture supernatant was determined.

For this purpose the strain was first of all incubated at 33° C. for 24 hours on agar plates with the appropriate antibiotic (brain-heart agar with kanamycin (25 mg/l)). A preculture was inoculated using this agar plate culture (10 ml medium in 100 ml Erlenmeyer flask). The full medium CgIII was used as medium for the preculture.

| Medium Cg III | |
|---|---|
| NaCl | 2.5 g/l |
| Bacto-Pepton | 10 g/l |
| Bacto-Yeast Extract | 10 g/l |
| Glucose (separately autoclaved) 2% (w/v) | |
| The pH was adjusted to pH 7.4 | |

Kanamycin (25 mg/l) was added to this medium. The pre-culture was incubated on a shaker for 16 hours at 33° C. and 240 rpm. A main culture was inoculated from this pre-culture so that the initial optical density (660 nm) of the main culture was 0.05. The medium MM was used for the main culture.

| Medium MM | |
|---|---|
| CSL (Corn Steep Liquor) | 5 g/l |
| MOPS (Morpholinopropanesulfonic acid) | 20 g/l |
| Glucose (separately autoclaved) | 50 g/l |
| $(NH_4)_2SO_4$ | 25 g/l |
| $KH_2PO_4$ | 0.1 g/l |
| $MgSO_4 \cdot 7 H_2O$ | 1.0 g/l |
| $CaCl_2 \cdot 2 H_2O$ | 10 mg/l |
| $FeSO_4 \cdot 7 H_2O$ | 10 mg/l |
| $MnSO_4 \cdot H_2O$ | 5.0 mg/l |
| Biotin (sterile filtered) | 0.3 mg/l |
| Thiamine.HCl (sterile filtered) | 0.2 mg/l |
| $CaCO_3$ | 25 g/l |

CSL, MOPS and the salt solution were adjusted with ammonia water to pH 7 and autoclaved. The sterile substrate and vitamin solutions as well as the dry autoclaved $CaCO_3$ were then added.

Cultivation takes place in a 10 ml volume in a 100 ml Erlenmeyer flask with baffles. Kanamycin (25 mg/l) was added. Cultivation was performed at 33° C. and 80% atmospheric humidity.

After 72 hours the OD was measured at a measurement wavelength of 660 nm using the Biomek 1000 (Beckmann Instruments GmbH, Munich). The amount of lysine formed was measured with an amino acid analyser from Eppendorf-BioTronik (Hamburg, Germany) by ion exchange chromatography and post-column derivatisation with ninhydrin detection.

The result of the test is shown in Table 1.

TABLE 1

| Strain | OD(660) | Lysine-HCl mg/l |
|---|---|---|
| C.glutamicum RES167 | 13.8 | 287 |
| C.glutamicum RES167/ pEC-K18mob2glkexp | 15 | 345 |

The following Figures are enclosed:

FIG. 1: Map of the plasmid pEC-K18mob2

FIG. 2: Map of the plasmid pEC-K18mob2glkexp

The acronyms and abbreviations used have the following meanings:

| | |
|---|---|
| per: | Gene for controlling the number of copies of pGA1 |
| oriV: | ColE1-like origin of pMB1 |
| rep: | Plasmid-coded replication region of C. glutamicum plasmid pGA1 |
| RP4mob: | RP4-mobilisation site |
| Kan: | Resistance gene for kanamycin |
| glk: | glk-gene of C.glutamicum |
| EcoRI: | Cleavage site of the restriction enzyme EcoRI |
| HindIII: | Cleavage site of the restriction enzyme HindIII |
| Ecl136II: | Cleavage site of the restriction enzyme Ecl136II |

What is claimed is:

1. A process for the fermentative production of L-lysine, comprising the following steps:
   (a) fermentation of the coryneform bacteria producing L-lysine, in which at least a glk gene comprising a nucleotide sequence encoding an amino acid sequence as set forth in SEQ ID NO: 2 is overexpressed,
   (b) enrichment of the L-amino acid in the medium or in the bacteria, and
   (c) isolation of the L-amino acid.

2. The process according to claim 1, wherein the *C. glutamicum* dapA gene encoding dihydrodipicolinate synthase is simultaneously overexpressed.

3. The process of claim 1, wherein the glk gene is overexpressed by increasing the copy number of said gene or by operably linking a promoter to said gene.

4. The process of claim 1, wherein the *C. glutamicum* lysE gene encoding a protein for lysine export is simultaneously overexpressed.

5. A process for the fermentative production of L-lysine, comprising the following steps:
   (a) fermentation of the coryneform bacteria producing L-lysine, in which at least a glk gene comprising a nucleotide sequence as set forth in SEQ ID NO: 1 is overexpressed,
   (b) enrichment of the L-amino acid in the medium or in the bacteria, and
   (c) isolation of the L-amino acid.

6. The process of claim 5, wherein said glk gene comprises nucleotides 461–1429 of SEQ ID NO: 1.

7. The process according to claim 5, wherein the *C. glutamicum* dapA gene encoding dihydrodipicolinate synthase is simultaneously overexpressed.

8. The process of claim 5, wherein the glk gene is overexpressed by increasing the copy number of said gene or by operably linking a promoter to said gene.

9. The process of claim 5, wherein the *C. glatamicum* lysE gene encoding a protein for lysine export is simultaneously overexpressed.

10. The process of claim 6, wherein the glk gene fragment is overexpressed by increasing the copy number of said gene fragment or by operably linking a promoter to said gene fragment.

* * * * *

SEQUENCE LISTING

<160> NUMBER OF SEQ ID NOS: 4

<210> SEQ ID NO 1
<211> LENGTH: 1540
<212> TYPE: DNA
<213> ORGANISM: Corynebacterium glutamicum
<220> FEATURE:
<221> NAME/KEY: CDS
<222> LOCATION: (461)..(1429)

<400> SEQUENCE: 1

```
aaattccttg gcgccttga atatcaagat atgatcaaca cgcttgccgc cgcagatatt      60
ttcgcgatgc cagcgcgcac ccgcggtggc ggacttgatg ttgaaggctt gggcattgtc     120
tatctcgagg cacaagcctg cggagtgccg gtgatagccg gcacctctgg cggcgcgcca     180
gagacggtga ctccggcaac tggcctggtt gtggaggggt cggacgtcga taagctgtct     240
gagcttttaa ttgagcttct cgacgatccg atccgccgcg ccgcgatggg cgctgcaggt     300
agggcgcatg tggaggccga atggtcgtgg gaaatcatgg gggagcggtt gaccaatatt     360
ttgcagagtg aaccacgatg atggttggac agctgttgat agctatactt tgaaagatta     420
aattcaccta atcctgtgt  agaacgcgag gggcactctt atg cca caa aaa ccg         475
                                              Met Pro Gln Lys Pro
                                                1               5 gcc agt ttc gcg gtg ggc ttt gac atc ggc ggc acc aac atg cga gcc       523
Ala Ser Phe Ala Val Gly Phe Asp Ile Gly Gly Thr Asn Met Arg Ala
            10                  15                  20 ggg ctt gtc gac gaa tcc ggg cgc atc gtg acc agt ttg tcg gcg ccg       571
Gly Leu Val Asp Glu Ser Gly Arg Ile Val Thr Ser Leu Ser Ala Pro
        25                  30                  35 tcg ccg cgc acg acg cag gca atg gaa cag ggg att ttt gat cta gtc       619
Ser Pro Arg Thr Thr Gln Ala Met Glu Gln Gly Ile Phe Asp Leu Val
    40                  45                  50 gaa cag ctc aag gcc gaa tac ccg gtt ggt gct gtg gga ctt gcc gtc       667
Glu Gln Leu Lys Ala Glu Tyr Pro Val Gly Ala Val Gly Leu Ala Val
55                  60                  65 gcg gga ttt ttg gat cct gag tgc gag gtt gtt cga ttt gcc ccg cac       715
Ala Gly Phe Leu Asp Pro Glu Cys Glu Val Val Arg Phe Ala Pro His
70                  75                  80                  85 ctt cct tgg cgc gat gag cca gtg cgt gaa aag ttg gaa aac ctt ttg       763
Leu Pro Trp Arg Asp Glu Pro Val Arg Glu Lys Leu Glu Asn Leu Leu
                90                  95                 100 ggc ctg cct gtt cgt ttg gaa cat gat gcc aac tca gcg gcg tgg ggt       811
Gly Leu Pro Val Arg Leu Glu His Asp Ala Asn Ser Ala Ala Trp Gly
            105                 110                 115 gag cat cgt ttt ggt gca gct caa ggc gct gac aac tgg gtt ttg ttg       859
Glu His Arg Phe Gly Ala Ala Gln Gly Ala Asp Asn Trp Val Leu Leu
        120                 125                 130 gca ctc ggc act gga att ggt gca gcg ctg att gaa aaa ggc gaa att       907
Ala Leu Gly Thr Gly Ile Gly Ala Ala Leu Ile Glu Lys Gly Glu Ile
    135                 140                 145 tac cgt ggt gca tat ggc acg gca cca gaa ttt ggt cat ttg cgt gtt       955
Tyr Arg Gly Ala Tyr Gly Thr Ala Pro Glu Phe Gly His Leu Arg Val
150                 155                 160                 165 gtt cgt ggc gga cgc gca tgt gcg tgt ggc aaa gaa ggc tgc ctg gag      1003
Val Arg Gly Gly Arg Ala Cys Ala Cys Gly Lys Glu Gly Cys Leu Glu
                170                 175                 180 cgt tac tgt tcc ggt act gcc ttg gtt tac act gcg cgt gaa ttg gct      1051
Arg Tyr Cys Ser Gly Thr Ala Leu Val Tyr Thr Ala Arg Glu Leu Ala
```

-continued

```
                                185                 190                 195
tcg cat ggc tca ttc cgc aac agc ggg ctg ttt gac aag atc aaa gcc        1099
Ser His Gly Ser Phe Arg Asn Ser Gly Leu Phe Asp Lys Ile Lys Ala
        200                 205                 210 gat ccg aat tcc atc aat gga aaa acg atc act gcg gca gcg cgc caa        1147
Asp Pro Asn Ser Ile Asn Gly Lys Thr Ile Thr Ala Ala Ala Arg Gln
215                 220                 225 gaa gac cca ctt gct ctc gcc gtt ctg gaa gat ttc agc gag tgg ctg        1195
Glu Asp Pro Leu Ala Leu Ala Val Leu Glu Asp Phe Ser Glu Trp Leu
230                 235                 240                 245 ggc gaa act ttg gcg atc att gct gat gtc ctt gac cca ggc atg atc        1243
Gly Glu Thr Leu Ala Ile Ile Ala Asp Val Leu Asp Pro Gly Met Ile
            250                 255                 260 atc att ggt ggc gga ctg tcc aat gct gcc gac ctt tat ttg gat cgc        1291
Ile Ile Gly Gly Gly Leu Ser Asn Ala Ala Asp Leu Tyr Leu Asp Arg
            265                 270                 275 tcg gtc aac cac tat tcc acc cgc atc gtc ggc gca gga tat cgc cct        1339
Ser Val Asn His Tyr Ser Thr Arg Ile Val Gly Ala Gly Tyr Arg Pro
            280                 285                 290 ttg gca cgc gtt gcc aca gct cag ttg ggt gcg gat gct ggc atg atc        1387
Leu Ala Arg Val Ala Thr Ala Gln Leu Gly Ala Asp Ala Gly Met Ile
    295                 300                 305 ggt gtc gct gat cta gct cga cgc tct gta gtg gaa gcc aac                1429
Gly Val Ala Asp Leu Ala Arg Arg Ser Val Val Glu Ala Asn
310                 315                 320 taggtgtttt tcggtgggct gcgatgacgc atgtccacca aaagagccac cccttaaaga     1489
aattaaaaag tggttttggt agcttcgcag caaaatacac atcgtgggta a              1540
```

<210> SEQ ID NO 2
<211> LENGTH: 323
<212> TYPE: PRT
<213> ORGANISM: Corynebacterium glutamicum

<400> SEQUENCE: 2

```
Met Pro Gln Lys Pro Ala Ser Phe Ala Val Gly Phe Asp Ile Gly Gly
1               5                   10                  15

Thr Asn Met Arg Ala Gly Leu Val Asp Glu Ser Gly Arg Ile Val Thr
                20                  25                  30

Ser Leu Ser Ala Pro Ser Pro Arg Thr Thr Gln Ala Met Glu Gln Gly
            35                  40                  45

Ile Phe Asp Leu Val Glu Gln Leu Lys Ala Glu Tyr Pro Val Gly Ala
        50                  55                  60

Val Gly Leu Ala Val Ala Gly Phe Leu Asp Pro Glu Cys Glu Val Val
65                  70                  75                  80

Arg Phe Ala Pro His Leu Pro Trp Arg Asp Glu Pro Val Arg Glu Lys
                85                  90                  95

Leu Glu Asn Leu Leu Gly Leu Pro Val Arg Leu Glu His Asp Ala Asn
                100                 105                 110

Ser Ala Ala Trp Gly Glu His Arg Phe Gly Ala Ala Gln Gly Ala Asp
            115                 120                 125

Asn Trp Val Leu Leu Ala Leu Gly Thr Gly Ile Gly Ala Ala Leu Ile
        130                 135                 140

Glu Lys Gly Glu Ile Tyr Arg Gly Ala Tyr Gly Thr Ala Pro Glu Phe
145                 150                 155                 160

Gly His Leu Arg Val Val Arg Gly Gly Arg Ala Cys Ala Cys Gly Lys
                165                 170                 175
```

```
-continued

Glu Gly Cys Leu Glu Arg Tyr Cys Ser Gly Thr Ala Leu Val Tyr Thr
            180                 185                 190

Ala Arg Glu Leu Ala Ser His Gly Ser Phe Arg Asn Ser Gly Leu Phe
        195                 200                 205

Asp Lys Ile Lys Ala Asp Pro Asn Ser Ile Asn Gly Lys Thr Ile Thr
    210                 215                 220

Ala Ala Ala Arg Gln Glu Asp Pro Leu Ala Leu Ala Val Leu Glu Asp
225                 230                 235                 240

Phe Ser Glu Trp Leu Gly Glu Thr Leu Ala Ile Ile Ala Asp Val Leu
                245                 250                 255

Asp Pro Gly Met Ile Ile Ile Gly Gly Gly Leu Ser Asn Ala Ala Asp
            260                 265                 270

Leu Tyr Leu Asp Arg Ser Val Asn His Tyr Ser Thr Arg Ile Val Gly
        275                 280                 285

Ala Gly Tyr Arg Pro Leu Ala Arg Val Ala Thr Ala Gln Leu Gly Ala
        290                 295                 300

Asp Ala Gly Met Ile Gly Val Ala Asp Leu Ala Arg Arg Ser Val Val
305                 310                 315                 320

Glu Ala Asn

<210> SEQ ID NO 3
<211> LENGTH: 18
<212> TYPE: DNA
<213> ORGANISM: PCR primer

<400> SEQUENCE: 3
actgacgtga gccagaac                                                         18

<210> SEQ ID NO 4
<211> LENGTH: 30
<212> TYPE: DNA
<213> ORGANISM: PCR primer

<400> SEQUENCE: 4
gatctatcta gacacctagt tggcttccac                                            30
```